US009486172B2

(12) United States Patent
Cobelli et al.

(10) Patent No.: US 9,486,172 B2
(45) Date of Patent: Nov. 8, 2016

(54) ESTIMATION OF INSULIN SENSITIVITY FROM CGM AND SUBCUTANEOUS INSULIN DELIVERY IN TYPE 1 DIABETES

(71) Applicants: Universita degli Studi di Padova; Mayo Foundation for Medical Education and Research, Rochester, MN (US)

(72) Inventors: Claudio Cobelli, Padua (IT); Chiara Dalla Man, Venice (IT); Michele Schiavon, Chioggia (IT); Ananda Basu, Rochester, MN (US); Yogish C. Kudva, Rochester, MN (US)

(73) Assignee: Università degli Studi di Padova, Padua (IT)

( * ) Notice: Subject to any disclaimer, the term of this patent is extended or adjusted under 35 U.S.C. 154(b) by 1027 days.

(21) Appl. No.: 13/661,755

(22) Filed: Oct. 26, 2012

(65) Prior Publication Data

US 2013/0211220 A1 Aug. 15, 2013

Related U.S. Application Data

(60) Provisional application No. 61/551,765, filed on Oct. 26, 2011.

(51) Int. Cl.
*A61B 5/145* (2006.01)
*A61B 5/00* (2006.01)
*A61B 5/1495* (2006.01)

(52) U.S. Cl.
CPC .......... *A61B 5/7278* (2013.01); *A61B 5/14532* (2013.01); *A61B 5/4839* (2013.01); *A61B 5/7275* (2013.01); *A61B 5/1495* (2013.01)

(58) Field of Classification Search
CPC ............ A61B 5/14532; A61B 5/1495; A61B 5/4839; A61B 5/7275; A61B 5/7278
See application file for complete search history.

(56) References Cited

U.S. PATENT DOCUMENTS

2010/0198520 A1* 8/2010 Breton ................ G06F 19/3431
702/19

FOREIGN PATENT DOCUMENTS

IL WO 2011016028 A1 * 2/2011 ......... A61B 5/14532

OTHER PUBLICATIONS

Medtronic Minimed, 2008, Paradigm® Veo™ User Guide.*
Shiang, The SAS Calculations of Areas Under the Curve (AUC) for Multiple Metabolic Readings, Presented on Oct. 15, 2004, Available online on Oct. 27, 2004 (p. 4).*
Steil et al, Evaluation of Insulin Sensitivity and B-Cell Function Indexes Obtained From Minimal Model Analysis of a Meal Tolerance Test, 2004, Diabetes, 53: 1201-1207.*

* cited by examiner

*Primary Examiner* — Jacqueline Cheng
*Assistant Examiner* — Angeline Premraj
(74) *Attorney, Agent, or Firm* — Bryan W. Bockhop; Bockhop Intellectual Property Law, LLC

(57) ABSTRACT

In a method of determining insulin sensitivity in a patient, glucose level is sensed continuously. A first area under the curve representing the glucose level over time is calculated. An amount of insulin that has been administered to the patient is sensed. An estimation of insulin on board the patient is calculated based on the glucose level and the amount of insulin administered to the patient. A second area under the curve representing the insulin on board over time is calculated. Patient data indicative of at least one patient physical parameter is received. Information indicative of amount of glucose ingested by the patient during a meal is received. An insulin sensitivity output indicative of ability of insulin to stimulate glucose utilization and inhibit glucose production in the patient based on the first and second area under the curve, the patient data and the meal information is generated.

9 Claims, 4 Drawing Sheets

US 9,486,172 B2

ESTIMATION OF INSULIN SENSITIVITY FROM CGM AND SUBCUTANEOUS INSULIN DELIVERY IN TYPE 1 DIABETES

CROSS-REFERENCE TO RELATED APPLICATION(S)

This application claims the benefit of U.S. Provisional Patent Application Ser. No. 61/551,765, filed Oct. 26, 2011, the entirety of which is hereby incorporated herein by reference.

BACKGROUND OF THE INVENTION

1. Field of the Invention

The present invention relates to medical systems and, more specifically, to a system for estimating insulin sensitivity.

2. Description of the Related Art

Diabetes is a chronic disease characterized by the inefficiency of the pancreas to produce insulin (type-1 diabetes, T1DM), or by malfunctions in both insulin secretion and action (type-2 diabetes, T2DM). As a result, in a diabetic subject the plasma glycaemic level exceeds the normal range, with several long and short term complications. Diabetes is taking on epidemic proportions with over 220 million individuals affected by this disease, a number which is expected to grow to 366 million by the year 2030. The rapid, constant increase of diabetic patients makes this disease one of the social-health emergencies of the third millennium. Most diabetics follow a metabolic monitoring therapy based on a combination of insulin injections and/or drugs, diet and physical exercise. The therapy is determined by the physician on the basis of glycaemia level measurements that the patient measures by him or herself in capillary blood 3 or 4 times a day (self-monitoring). This approach presents inevitable shortcomings due to the low amount of glycaemia data available related to the high glycaemia range during the day. Due to the shortcomings of the monitoring system, glycaemia may exceed normal limits (between 70 and 180 mg/dL). Hyperglycaemia, a situation in which the concentration of glucose in blood is higher than 180 mg/dL, causes various long-term complications such as cardiovascular disease, hypertension, retinopathies, etc.; while on the short-term, hypoglycaemia, glucose concentration lower than 70 mg/dL, may even be more dangerous, e.g. it may lead to diabetic coma, also because it may be difficult for the patient to recognize, particularly at night.

Extensive studies, including the Diabetes Control and Complications Trial (DCCT), have repeatedly demonstrated that the most effective way to prevent long-term complications of T1DM and T2DM is by maintaining BG levels within a normal range using intensive therapy. However, the same studies have also documented adverse effects of intensive therapy, the most acute of which is the increased risk of hypoglycemia which can brings also to coma and death. On one hand, intensive therapy could lead to improve metabolic control and reduce complications in T1DM and T2DM; on the other, intensive therapy was associated with an increase in hypoglycemia events. Thus, people with diabetes face the long-life optimization problem of maintaining strict metabolic control without increasing their risk of hypoglycemia.

The standard therapy, especially for T1DM, is based on multiple daily injection of insulin (bolus and basal doses), diet and physical exercise, tuned according to self-monitoring of blood glucose (SMBG) levels 3-4 times a day. However, in the last 10 years, new possibilities in diabetes therapy have been opened thanks to the availability of continuous glucose monitoring (CGM) sensors and insulin delivery systems, which substitute self-monitoring blood glucose (SMBG) and multiple daily injection therapy (MDI), respectively.

New noninvasive or minimally-invasive CGM devices can compensate the lack of information of the traditional 3-4 self-monitoring blood glucose (SMBG) measurements: in fact, they can measure, in real-time, the glycaemia level at continuous time (from every 1 to 5 minutes, according to the sensor) for up to several days (from 3 to 7 days, according to the technology), allowing the improvement of diabetes management. The most widespread insulin delivery systems are subcutaneous, but in a lesser extent also the intraperitoneal way is used even if nowadays it's a complex technology to be applied in everyday life, which, differently from multiple daily injection therapy, allows one to generally intensify insulin therapy with a reduced intrinsically associated high rate of hypoglycemia, improving diabetes management. Conventional insulin pumps can deliver insulin to the patient and can be configured to deliver rapid-acting insulin 24 hours a day: the total daily dose of insulin (TDI) can be divided into basal rates, continuously delivered over 24 hours keeping the blood glucose concentration levels in normal desirable range between meals as well as overnight which can be pre-programmed or manually changed according to various daily activities of the patient; and bolus doses, delivered before meals, to counteract carbohydrate's loads, or during episodes of high blood glucose concentration levels to bring glycaemia to normal desirable range.

In order to correctly evaluate the amount of insulin which should be present in the administered bolus, it would be fundamental to know the value of insulin sensitivity (SI), which corresponds to the ability of insulin to stimulate glucose utilization and inhibit glucose production. In fact, the knowledge of patient specific SI and its daily variation will help in determining optimal insulin treatment. Several indexes have been published, but the two most important have been favored in the past 3 decades: the clamp insulin sensitivity, SIDF, defined by DeFronzo as the ratio of glucose injection and insulin concentration during the hyperinsulinemic euglycemic clamp and the insulin sensitivity, SIBC, defined by Bergman and Cobelli which uses minimal model of glucose regulation during an intravenous glucose tolerance test (IVGTT).

Recently, several methods for determining insulin sensitivity from oral glucose tolerance test (OGTT) or meal test (MTT) have been proposed, but the difficulty with oral tests is that the input of the system (rate of glucose appearance) is unknown. An approach to simultaneously identifying parameters describing glucose absorption and insulin sensitivity using seven or more blood samples from MTT or OGTT has been developed by Dalla Man et al. and was validated against multiple tracer methods in non-diabetic subjects and results were well correlated with results from hyperinsulinemic clamps. However, this method requires at least seven blood samples to measure plasma glucose and insulin concentrations and the identification of a model with a sophisticated modeling software. Caumo et al. derived an index of insulin sensitivity with an integral approach, but it also requires frequent measurements of plasma glucose and insulin concentration after the meal; moreover, the method requires that both glucose and insulin concentrations have returned to basal values at the end of the experiment. This is a big limitation, since, in type 1 diabetic subjects, it is not unusual that glucose does not return to pretest glycemic basal value due to errors in insulin administration.

Other more empiric methods for determining insulin sensitivity from OGTT have also been proposed. Stumvoll et al. empirically obtained an insulin sensitivity index based on glucose and insulin measurements during an OGTT that was correlated with the glucose infusion rate during a hyperinsulinemic clamp. Matsuda et al. developed a composite insulin sensitivity index based on both fasting and mean values of glucose and insulin and showed that this measure was correlated with results from an hyperinsulinemic clamp. Hansen et al. empirically determined measures of insulin sensitivity from OGTT that were correlated with SI measured by IVGTT. However, all of them use plasma measurements. A new empiric approach to evaluate insulin sensitivity has been proposed by Breton and Kovatchev. It employs routine self-monitoring blood glucose (SMBG) data, collected over a period of 2-6 weeks and it is based on the theory of risk analysis of blood glucose data, combined with basic patient measurements. This method has the advantage to be easy to implement and uses simple data collected in normal daily life conditions, but, due to the long-time collected data, this not takes into account the intraday variability of this index which can be present in person's natural environment.

Therefore, there is a need for a method to estimate insulin sensitivity by using new technologies such as continuous glucose monitoring and subcutaneous insulin infusion devices which provide much more information about patient conditions respect to other devices. The goal of this invention is to use these new minimally-invasive technologies to estimate this fundamental parameter to optimize the control therapy in type 1 diabetes.

SUMMARY OF THE INVENTION

The present invention has several advantages over current methods to estimate insulin sensitivity in type 1 diabetes due to its easy implementation in normal daily life and the possibility to reevaluate this important parameter automatically after each meal for optimizing diabetes management. This invention is based on two fundamental components that are becoming even more used in type 1 diabetic patients:
  Continuous glucose monitoring (CGM) device which compensates the lack of information of the traditional self-monitoring blood glucose (SMBG) device by continuous measuring the glycaemia level. Moreover, to improve the quality of CGM data, the system may be integrated with calibration algorithms (which takes into account the BG-to-IG kinetics present between the interstitial and plasma compartments), when SMBG data are available.
  Continuous subcutaneous insulin infusion (CSII) device which, differently from multiple daily injections, is programmed by the user to infuse the insulin basal rate to supply the background insulin needs all day long and specified pre-meal boluses to cover meals.

The principal embodiment of the present invention is represented by a method for computing an estimate of insulin sensitivity (SI) by integration of CGM and CSII data, with basic measurements of the patient, for each meal during the day. Moreover, a direct possible application, which is already implemented in some insulin pumps, could be a bolus calculator based on inputs of meal carbohydrate content and glucose levels of the patient.

In one embodiment, the invention provides a fully autonomous system, which can be easily implemented in the artificial pancreas architecture already composed by instruments necessary to evaluate this parameter, thus improving the control therapy, by registering insulin sensitivity pattern during the day.

The disadvantages of the prior art are overcome by the present invention which, in one aspect, is a device for calculating insulin sensitivity in a patient, including a glucose module that includes a continuous glucose monitoring sensor configured to generate a glucose signal indicative of a glucose level in the patient and an area under the curve calculator that is responsive to the glucose signal and that generates a first area under the curve indicative of an area under a curve representing the glucose signal over a predetermined period of time. An insulin module is responsive to the glucose signal and to an insulin input from an insulin infusion device. The insulin input indicates an amount of insulin that has been administered to the patient by the insulin infusion device. The insulin module also includes an area under the curve calculator that generates a second area under the curve indicative of an area under a curve representing the insulin signal over a predetermined period of time. A patient module generates a patient data signal indicative of at least one patient physical parameter and a meal information signal indicative of an amount of glucose ingested by the patient during a meal. An insulin sensitivity calculator generates an insulin sensitivity output that is indicative of an ability of insulin to stimulate glucose utilization and inhibit glucose production in the patient based on the first area under the curve, the second area under the curve, the patient data signal and the meal information signal.

In another aspect, the invention is a system for calculating an insulin bolus dosage of insulin to be administered to the patient. A continuous glucose monitoring sensor is configured to generate a glucose signal indicative of a glucose level in the patient. An area under the curve calculator is responsive to the glucose signal and that generates a first area under the curve indicative of an area under a curve representing the glucose signal over a predetermined period of time. An insulin infusion device generates an insulin input indicative of an amount of insulin that has been administered to the patient. An insulin on board module is configured to generate an estimation of the insulin on board the patient based on the glucose signal and the insulin signal. An area under the curve calculator generates a second area under the curve indicative of an area under a curve representing the insulin on board over a predetermined period of time. A patient module generates a patient data signal indicative of at least one patient physical parameter and a meal information signal indicative of an amount of glucose ingested by the patient during a meal. An insulin sensitivity calculator generates an insulin sensitivity output that is indicative of an ability of insulin to stimulate glucose utilization and inhibit glucose production in the patient based on the first area under the curve, the second area under the curve, the patient data signal and the meal information signal. A bolus calculator is responsive to the insulin sensitivity output and is configured to generate the estimated bolus dosage of insulin to be administered to the patient.

In yet another aspect, the invention is a method of determining insulin sensitivity in a patient, in which a glucose level in the patient is sensed continuously. A first area under the curve indicative of an area under a curve representing the glucose level over a predetermined period of time is calculated. An amount of insulin that has been administered to the patient by an insulin infusion device is sensed. An estimation of insulin on board the patient is calculated based on the glucose level and the amount of insulin that has been administered to the patient. A second area under the curve indicative of an area under a curve representing the insulin on board over a predetermined period of time is calculated. Patient data indicative of at least one patient physical parameter is received. Meal information indicative of an amount of glucose ingested by the patient during a meal is also received. An insulin sensitivity output that is indicative of an ability of insulin to stimulate glucose utilization and inhibit glucose production in the patient based on the first area under the curve, the second area under the curve, the patient data and the meal information is generated.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
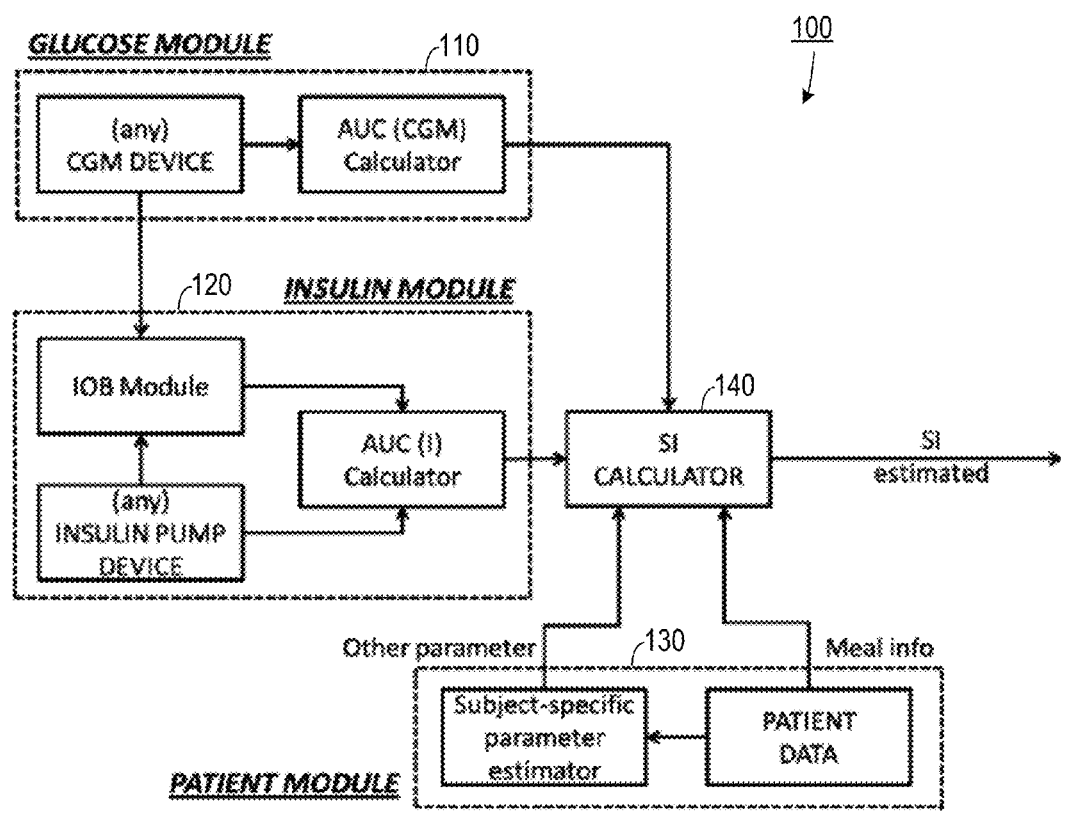
FIG. 1 is a schematic diagram showing a representative embodiment of the present invention.

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

All metabolic parameters change over time, thus from a long-time collected data it is not possible to provide a good estimation of these quantities for optimizing the treatment therapy of a T1DM patient. This is particularly true for insulin sensitivity because it usually changes with the time of day and with the activities of a person. Therefore it's necessary to define methods for tracking the changes in insulin sensitivity for the day-to-day optimization of diabetes control. However, the classic methods of estimation of SI require invasive hospital-based interventions, with blood sampling for insulin and glucose. Due to the impossibility to perform these procedures during normal daily life conditions, it is important to find a way to derive insulin sensitivity and other metabolic parameters from readily available data collected during everyday life, such as continuous glucose monitoring data (CGM) and continuous subcutaneous insulin infusion (CSII) devices, combined with easily accessible personal parameters.

As shown in FIG. 1, one representative embodiment of the invention 100 includes four components: a glucose module 110, an insulin module 120, a patient module 130 and an SI calculator 140.

The glucose module 110 considers continuous glucose monitoring data $$\left[\frac{mg}{dL}\right],$$

from the start of the meal until six hours later (the time at which the glucose absorption of the meal is assumed to be ended) and calculates the area under the curve (AUC) with the trapezoidal rule. If present, at least two SMBG references could be used for the calibration of CGM signal (as shown in greater detail in FIG. 2) by using a calibration module to combine the data from the sensors.

The insulin module 120 considers the subcutaneous insulin infusion data [mU/min] from three hours before the start of the meal, to take into account, by using an Insulin on Board algorithm, the delayed effect of insulin correction boluses administered before the pre-meal bolus, till six hours later and calculates area under the curve.

The patient module 130 includes the knowledge of the amount of glucose ingested during the meal (D) [mg], patient specific parameters, such as: body weight (BW) [kg], age and height [m], for the estimation of the subject-specific parameter clearance (CL) [L/min], and parameters of glucose kinetics fixed to population values, such as: glucose effectiveness at zero insulin $$(GEZ_I)\left[\frac{dL}{(min \cdot kg)}\right];$$

fraction of the ingested glucose which appears in the systemic circulation (f); and volume of glucose distribution $$(V_G)\left[\frac{dL}{kg}\right].$$

The SI calculator 140 employs a simple integral approach, without the need to solve any differential equation, to evaluate the insulin sensitivity by using simple algebra. This method robustly identifies differences in insulin sensitivity in type 1 diabetes during the day. In fact the insulin sensitivity measurements obtained are well correlated with results from minimal model estimation of insulin sensitivity from oral test (r>0.8).

Figure 2:
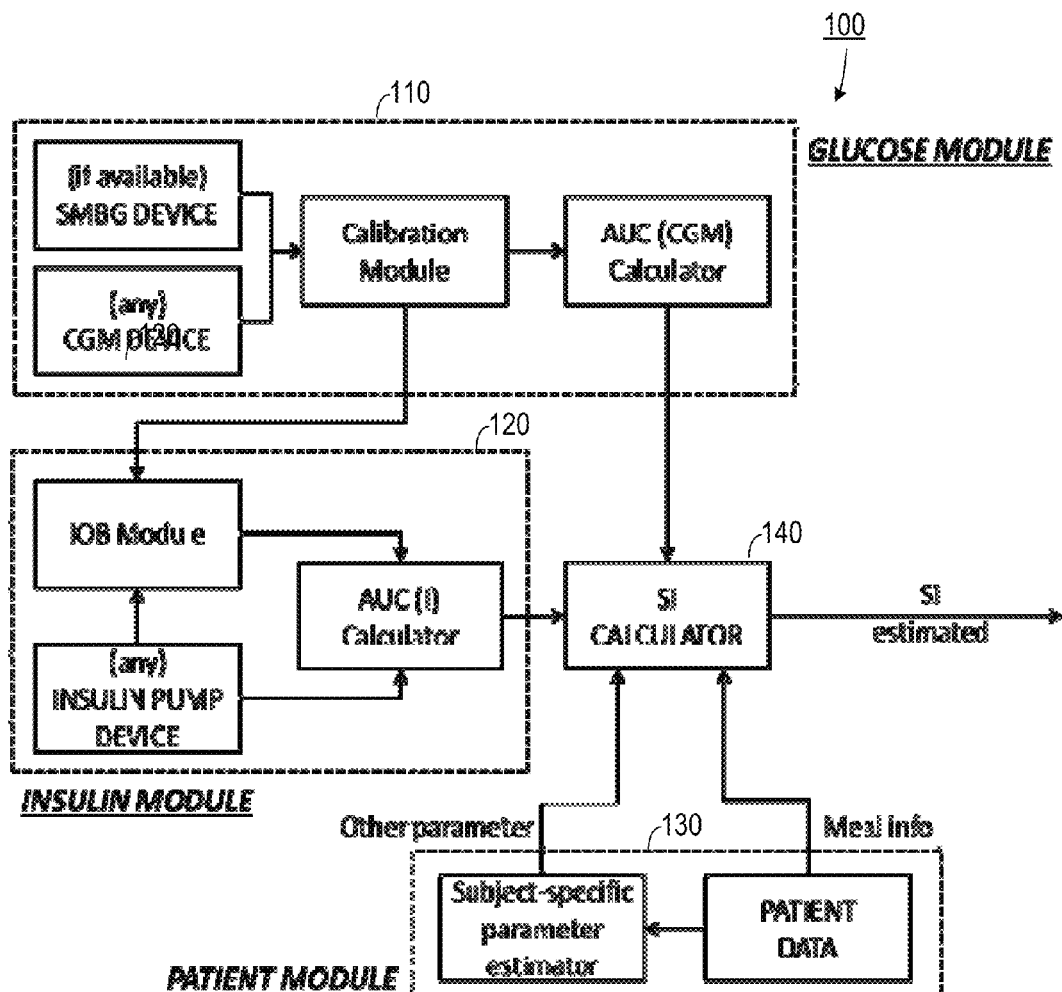
FIG. 2 is a schematic showing the embodiment shown in FIG. 1, integrated with a calibration module (where SMBG data is available).

In the following sections the descriptions of the principal components of the invention, as shown in FIGS. 1 and 2.

Glucose Module

Considering that interstitial glucose is only a delayed version of plasma glucose (except for calibration errors) due to BG-to-IG kinetics, from an integral point of view, CGM signal can be used as plasma glucose signal. Thus, we can compute the area under the curve (AUC) of over basal CGM data AUC(☐CGM), instead of AUC of above basal plasma glucose, using the trapezoidal rule (CGM sample at start of the meal is used as basal). Similarly, we can compute the AUC of the absolute value of the over basal continuous glucose monitoring data AUC(|☐CGM|), instead of the AUC of absolute value of the over basal plasma glucose. It is of note that, if CGM exhibits an excursion (or more) below the pretest basal level, defining t_cross the time when CGM crosses the baseline level (evaluated by linearly interpolating the CGM samples that immediately precede and follow the crossing baseline CGM level), we can compute the always positive area under the curve by separation of the two integrals.

To exclude calibration errors, if at least two SMBG samples are available, it is possible to automatically calibrate the CGM signal to improve its quality (as shown in FIG. 2). This operation may be implemented with a simple algorithm which takes into account the BG-to-IG kinetics present between the interstitial and plasma compartments. Other calibration algorithms can also be employed.

Insulin Module

Assuming that all infused insulin eventually reaches the blood stream, the integral of plasma insulin can be obtain from subcutaneous insulin infusion divided by the plasma insulin clearance, which can be approximated using field-measurable subject characteristics (see Patient Module). The plasma insulin kinetics, regardless of the model of subcutaneous absorption, is:

$$I(t) = -n \cdot I(t) + \frac{Inf(t)}{V_I}$$

where I(t) is the plasma insulin concentration, Inf(t) is the insulin infusion, $V_I$ is the volume of insulin distribution and n is the fractional insulin clearance rate ($n = CL/V_I$).

Then, integrating this differential equation and assuming that at the end of the study plasma insulin has recovered to basal value, we find $$\int_{t_{meal}}^{t_{end}} I(t)dt = -n \cdot \int_{t_{meal}}^{t_{end}} I(t)dt + \int_{t_{meal}}^{t_{end}} \frac{Inf(t)}{V_I} dt$$

$$0 = -n \cdot \int_{t_{meal}}^{t_{end}} I(t)dt + \int_{t_{meal}}^{t_{end}} \frac{Inf(t)}{V_I} dt$$

$$\int_{t_{meal}}^{t_{end}} I(t)dt = \frac{1}{n \cdot V_I} \cdot \int_{t_{meal}}^{t_{end}} Inf(t)dt = \frac{1}{CL} \int_{t_{meal}}^{t_{end}} Inf(t)dt$$

where $t_{meal}$ is the time of pre-meal bolus and $t_{end}$ is the ending time of the study and where $CL = n \cdot V_I$ is the clearance, with n fractional clearance rate and $V_I$ volume of insulin distribution. Thus we can compute the area under the curve (AUC) of plasmatic insulin, starting from the knowledge of the subcutaneous insulin infusion:

$$AUC(I) = \frac{1}{CL} \cdot \int_{t_{meal}}^{t_{end}} \text{basal}(t)dt + \sum_{t_i=t_{meal}}^{t_{end}} \left[\frac{\text{bolus}(t_1)}{CL}\right]$$

where bolus is the pre-meal bolus and all correction boluses delivered during the integration period and basal corresponds to the basal insulin rate during the same period.

As previously mentioned, if correction boluses are administered before the start of the meal, we have to consider that their contribution could be still active insulin in the blood stream. We can estimate the residual active insulin, by using a simple algorithm which calculates the Insulin on Board and add this quantity, as an insulin bolus, to the AUC(I) previously estimated. Moreover, if correction boluses are administered before the end of the considered interval, this algorithm is used to evaluate the still active insulin in the blood stream at the end of the study, which is subtracted to the AUC(I) previously estimated.

$$AUC(I) = \frac{1}{CL} \cdot \int_{t_{meal}}^{t_{end}} \text{basal}(t)dt + \sum_{t_i=t_{meal}}^{t_{end}} \left[\frac{\text{bolus}(t_i)}{CL}\right] + IOB(I_{pre-meal}) - IOB(I_{post-meal})$$

Patient Module

This module provides first the information about the meal, given by the patient. Then, it is necessary to estimate the plasma insulin clearance (CL), for each subject, which can be approximated using field-measurable subject characteristics as follows:

$$BSA = 0.007194 \cdot \text{height}^{0.725} \cdot \text{weight}^{0.425}$$

$$CL = \exp[-0.0402 + 0.372 \cdot BSA - 1.00313 \cdot \text{age}]$$

where BSA [m²] stands for body surface, and height [m], weight [kg] and age [years] stand for the height, weight and age of the subjects, respectively. The remaining parameters, as defined before, are fixed to population value. Specifically:

$$GEZI = 0.01 \text{ dL/(min·kg)}$$

$$f = 0.9$$

$$V_G = 1.48 \text{ dL/kg}$$

SI Calculator

Once, all elements and parameters which contribute to the estimation of insulin sensitivity have been defined, insulin sensitivity can be calculated as:

$$SI = \frac{\frac{D \cdot f}{BW} - GEZI \cdot AUC(\Delta CGM) - V_G \cdot [CGM(t_{end}) - CGM(t_{meal})]}{AUC(I) \cdot \left[\frac{AUC(|\Delta CGM|)}{(t_{end} - t_{meal})}\right]}$$

This formula is derived from integration of the minimal model with some opportune approximations to simplify integral calculations. As a result, SI is the ratio between two terms. In the numerator appears the term (D·f/BW), from which the glucose excursion at the end of the study ($V_G \cdot [CGM(t_{end}) - CGM(t_{meal})]$) and the effect of glucose in its disappearance ($GEZI \cdot AUC(\Delta CGM)$) are subtracted. In the denominator there is the total insulin infused to the patient multiply to the average of the absolute value of CGM signal excursion, which modulates the effect of insulin to the glycemic excursion. It is worth noting that, if glucose presents excursion above/below the glycemic basal value, it has negative/positive effect in the numerator because either effect of glucose on its disappearance and the glucose excursion at the end of the study increase/reduce their value, which means that SI value decreases/increases. On the contrary, in the denominator this effect does not depend on where the glycemic excursion is (above or below the glycemic basal value), indeed it modulates, in absolute value, the SI value with the total insulin infused.

Figure 3:
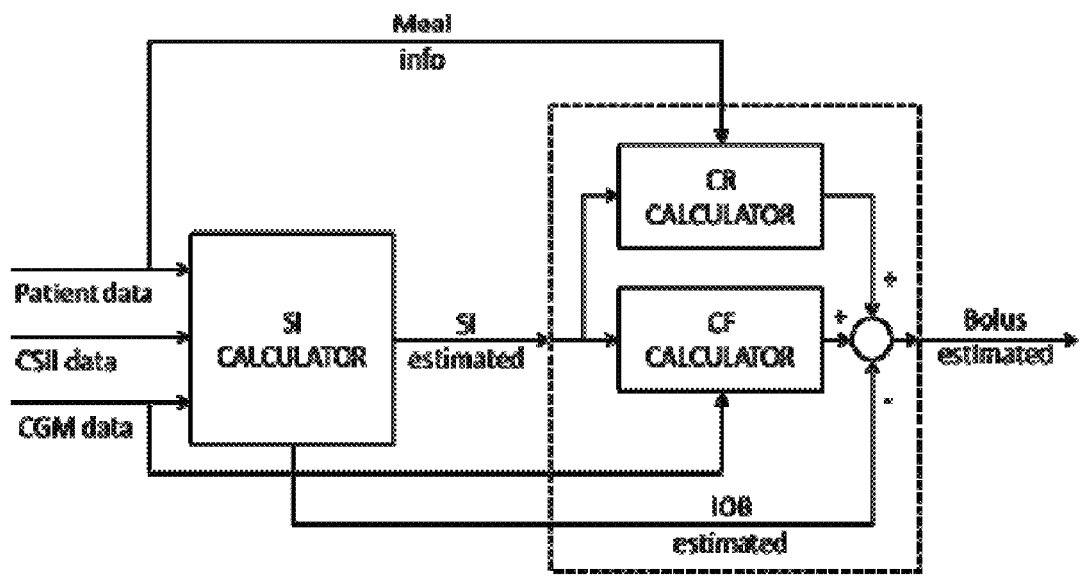
FIG. 3 is a schematic of an application based on the present invention.

In the following section a possible application of the present invention (as show in FIG. 3) is described.

One application of the present invention is its employment in a BOLUS CALCULATOR MODULE, that could be useful to improve the patient insulin therapy. In fact, a bolus calculator module uses calculators of the insulin to carbs ratio (CR), the correction factor (CF) and the insulin on board (IOB).

Bolus Calculator Module

The recommended bolus is the insulin bolus which has the role to counteract carbohydrate loads and/or to bring glycaemia to normal desirable range if episodes of high blood glucose levels occur:

$$\text{recommended bolus} = \frac{\text{meal dose}}{CR} + \frac{\Delta(\text{glucose})}{CF} - IOB$$

where meal dose is the amount of glucose ingested during the meal and Δglucose is the glycemic excursion between the pre-meal and target glycemic value. CR and CF are usually time-varying parameters which patient adjusts on physician's advice based on last weeks of patient's diary. However, these parameters could be exactly calculated if only patient's insulin sensitivity index is known.

CR Calculator

Optimal CR [g/U] is computed based on the following consideration. In order to obtain an optimal pre-meal bolus we have to equal the total amount of glucose entering the system after a meal to the total amount of glucose cleared due to the pre-meal bolus. This is equivalent to equating the integrals of the rate of appearance and the glucose cleared by insulin action:

$$\frac{D \cdot f}{BW} = SI \cdot \frac{\text{bolus}}{CL} \cdot \frac{(glucose_{max} + glucose_{target})}{2}$$

where D is the amount of glucose ingested during the meal, f is the fraction of the ingested glucose which appears in the systemic circulation, BW is the body weight, CL is the plasma insulin clearance, $glucose_{max}$ is the maximum tolerated glycemic value and $glucose_{target}$ is the target glycemic value.

Thus, one can calculate CR as:

$$CR = \frac{D}{\text{bolus}} = \frac{SI \cdot BW}{f \cdot CL} \cdot \frac{(glucose_{max} + glucose_{target})}{2}$$

CF Calculator

The correction factor [mg/dL/U] represents the decrease in glucose concentration caused by 1U insulin bolus. Thus by equating the observed difference between glucose concentration to patient glucose target and the amount of glucose cleared by an insulin correction bolus:

$$V_G \cdot \Delta\text{glucose} = SI \cdot \frac{\text{bolus}}{CL} \cdot \frac{(glucose_{start} + glucose_{target})}{2}$$

where $\Delta\text{glucose} = glucose_{start} - glucose_{target}$, with $glucose_{start}$ the glycemic value at the start of the study and $glucose_{target}$ the target glycemic value. Thus, one can calculate CF as:

$$CF = \frac{\Delta\text{glucose}}{\text{bolus}} = \frac{SI}{CL \cdot V_G} \cdot \frac{(glucose_{start} + glucose_{target})}{2}$$

Insulin on Board (IOB) can be easily estimated by the IOB module which uses the insulin infusion information given by the subcutaneous insulin infusion device.

Validation

In one experimental embodiment, the CGM/CSII-based estimate of SI was validated via comparison with reference measurements of SI obtained by minimal model method using plasma glucose and insulin data collected during triple-tracer protocol with standard mixed meal. Twelve type 1 diabetic subjects (unpublished data) were studied for three days in hospital. Randomly once a day, a triple-tracer protocol with standard mixed meal was performed and frequent blood samples were drawn for measurement of plasma glucose and insulin concentrations in order to estimate SI with the minimal model, considered as reference. At the same time, subjects wore both subcutaneous insulin pump and CGM in order to estimate SI with the present invention.

Figure 4:
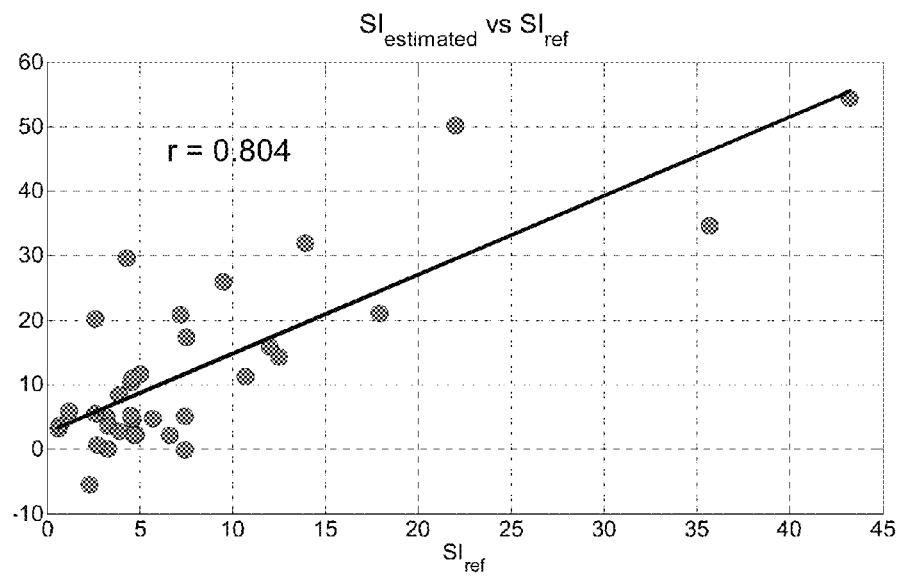
FIG. 4 is a graph showing a correlation between SI obtained from the invention (using parameters calculated by the Patient module), and reference SI, derived with minimal model from plasma concentrations.
Figure 5:
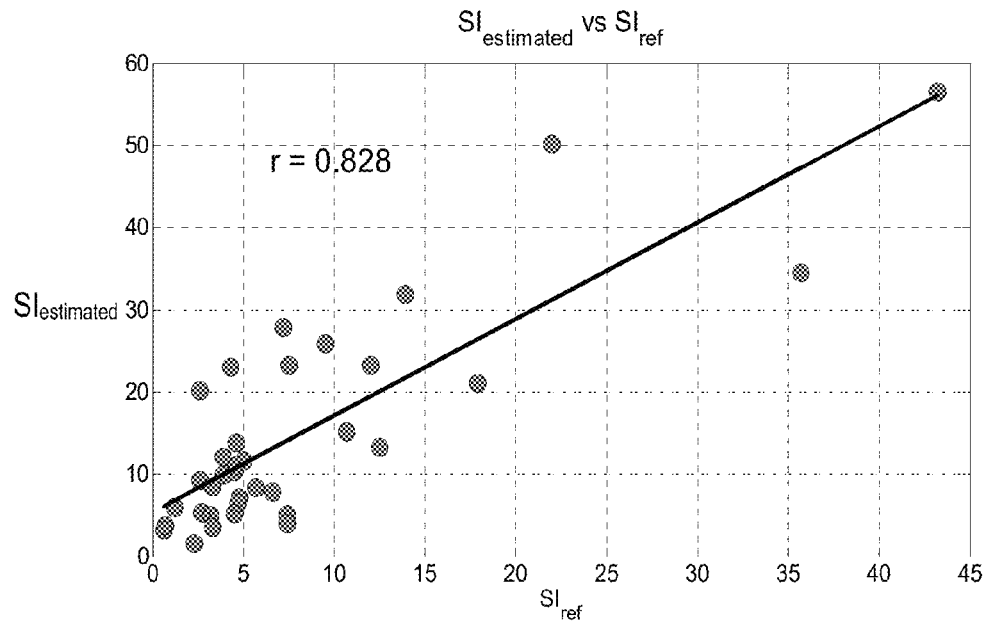
FIG. 5 is a graph showing a correlation between SI obtained from the invention (with parameters calculated by the Patient module, but with patient specific GEZI) and reference SI, derived with minimal model from plasma concentrations.

As shown in FIG. 4, there is good correlation r=0.804 ($p<10^{-8}$) between the reference SI, estimated with the minimal model, and SI estimated by the invention, with parameters GEZI, f and $V_G$ fixed to population values and CL approximated using field-measurable subject characteristics. One can note that few SI estimated by the invention result negative. These values are associated to subjects who did not return to pretest glycemic basal value, but continued to rise even long time after the meal. This is probably caused by too small pre-meal insulin bolus which is not able to compensate the total amount of glucose entering the system after the meal. The large above basal CGM makes the term GEZI·AUC(ΔCGM) very large, since parameter GEZI was fixed to population value. In order to test the effect of fixing GEZI to a wrong value, we check the estimates of SI with GEZI individualized for each patient (using the value estimated with the minimal model). Comparison with reference SI is shown in FIG. 5. Correlation between the two indices becomes r=0.831 ($p<10^{-9}$).

Figure 6:
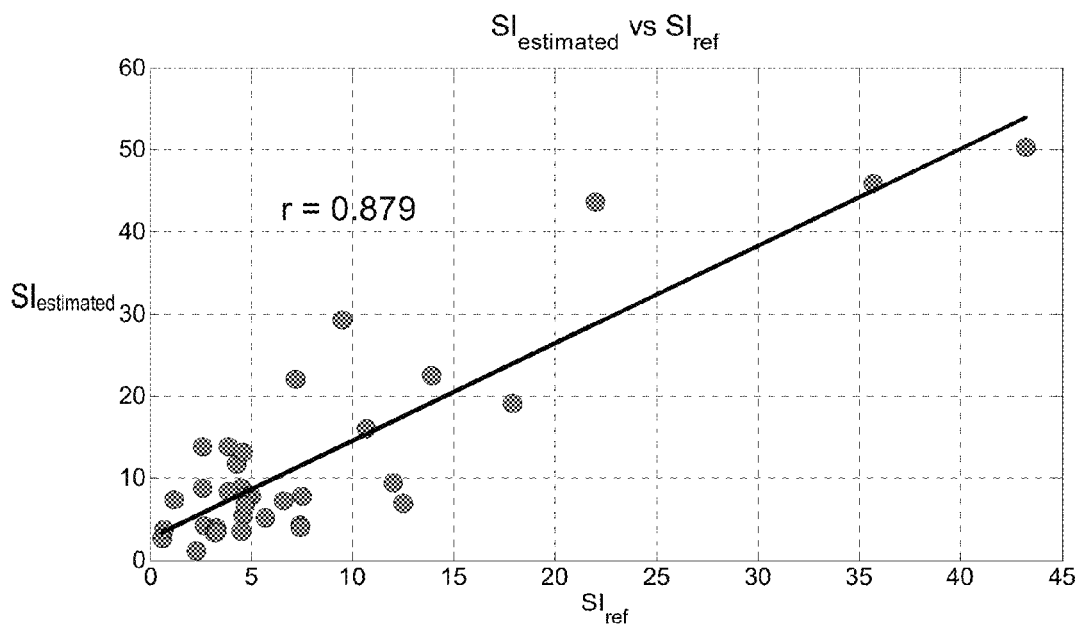
FIG. 6 is a graph showing a correlation between SI obtained from the invention (with parameters calculated by the Patient module, but with patient specific GEZI and CL) and reference SI, derived with minimal model from plasma concentrations.

In order to test the effect of fixing CL using the population modelError! Reference source not found, we also calculate SI using individualized GEZI and CL, this last extracted directly from the data for each patient. Comparison with reference SI is shown in FIG. 6. Correlation between the two indices becomes r=0.881 ($p<10^{-11}$).

However, these last two SI estimates cannot be obtained in normal life conditions, because usually we have no access to individualized GEZI and CL. These results are useful to demonstrate that by using subject-specific parameters the indexes estimated are closer to the reference values.

In summary, insulin sensitivity is one of the most important individual parameter for optimizing control therapy in type 1 diabetes. However, so far methods to estimate this index by using new minimally-invasive technologies such as continuous glucose monitoring and subcutaneous insulin infusion devices have never been proposed. With this invention we provide an estimation of this index after each meal, allowing one to assess its changes during the day. This was not possible with available techniques, which allow either to estimate SI with invasive measurements, or to estimate it with data available in normal daily life but not as frequently as with this invention.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A device for calculating insulin sensitivity in a patient, comprising:
   (a) a glucose module that includes a continuous glucose monitoring sensor configured to generate a glucose signal (CGM signal) indicative of a glucose level in the patient and an area under the curve calculator that is responsive to the glucose signal and that generates a first area under the curve signal [AUC($\Delta$CGM)] indicative of an area under the curve representing the over basal glucose signal and a second area under the curve signal [AUC(|$\Delta$CGM|)] indicative of an area under the curve representing the absolute value of over basal glucose signal over a predetermined period of time;
   (b) an insulin module that is responsive to the glucose signal and to an insulin input from an insulin infusion device, the insulin input indicative of an amount of insulin that has been administered to the patient by the insulin infusion device, the insulin module also including an area under the curve calculator that generates an insulin module area under the curve [AUC(I)] indicative of an area under a curve representing the insulin signal over a predetermined period of time. the insulin module also including an insulin on board (IOB) module that is responsible for adding a contribution of onboard still active insulin administered before the predetermined period of time and subtracting the contribution of still active insulin at the end of the predetermined period of time;
   (c) a patient module that generates a patient data signal indicative of at least one patient physical parameter and a meal information signal indicative of an amount of glucose ingested by the patient during a meal; and
   (d) an insulin sensitivity calculator that generates an insulin sensitivity output that is indicative of an ability of insulin to stimulate glucose utilization and inhibit glucose production in the patient based on the first area under the curve [AUC($\Delta$CGM)] and the second area under the curve [AUC(|$\Delta$CGM|)] signals generated by the glucose module, the insulin module area under the curve [AUC(I)], the patient data signal and the meal information signal, wherein the insulin sensitivity output (SI) is calculated as follows:

$$SI = \frac{\frac{D \cdot f}{BW} - GEZI \cdot AUC(\Delta CGM) - V_G \cdot [CGM(t_{end}) - CGM(t_{meal})]}{AUC(I) \cdot \left[\frac{AUC(|\Delta CGM|)}{(t_{end} - t_{meal})}\right]}$$

where:
   D=amount of glucose ingested during the meal (in mg);
   f=0.9;
   BW=patient's body weight (in kg);
   GEZI=a population parameter fixed to 0.01 dL/kg/min;
   $V_G$=1.48 dL/kg;
   $t_{end}$=ending time of study;
   $t_{meal}$=starting time of study corresponding to time of the patient's last meal;
   CGM($t_{end}$)=value of CGM signal at ending time of study; and
   CGM($t_{meal}$)=value of CGM signal at starting time of study corresponding to time of last meal.

2. The device of claim 1, wherein the continuous glucose monitoring sensor comprises a self-monitoring blood glucose device.

3. The device of claim 2, wherein the continuous glucose monitoring sensor further comprises a calibration module configured to combine data from both the self-monitoring blood glucose device and the continuous glucose monitoring sensor so as to generate the glucose signal.

4. The device of claim 1, further comprising a bolus calculator module that is responsive to the insulin sensitivity output and that is configured to generate an estimated bolus dosage of insulin to be administered to the patient.

5. The device of claim 4, wherein the bolus calculator module comprises:
   (a) a carbs ratio calculator configured to calculate a carbs ratio representing a total amount of glucose entering the patient after a meal to the total amount of glucose cleared due to a pre-meal bolus;
   (b) a correction factor calculator configured to calculate a correction factor representing a decrease in glucose in the patient caused by an insulin bolus; and
   (c) an adding circuit that adds the carbs ratio to the correction factor and that subtracts an estimated insulin on board to generate an estimated bolus dosage value.

6. A system for calculating an estimated bolus dosage of insulin to be administered to a patient, comprising:
   (a) a continuous glucose monitoring sensor configured to generate a glucose signal (CGM signal) indicative of a glucose level in the patient and an area under the curve calculator that is responsive to the glucose signal and that generates a first area under the curve signal [AUC($\Delta$CGM)] indicative of an area under the curve representing the over basal glucose signal and a second area under the curve signal [AUC(|$\Delta$CGM|)] indicative of an area under the curve representing the absolute value of over basal glucose signal over a predetermined period of time;
   (b) an insulin infusion device, responsive to the basal glucose signal and to an insulin input from an insulin infusion device, the insulin input indicative of an amount of insulin that has been administered to the patient by the insulin infusion device, the insulin module also including an area under the curve calculator that generates an insulin module area under the curve [AUC(I)] indicative of an area under a curve representing the insulin signal over a predetermined period of time. the insulin module also including an insulin on board (IOB) module that is responsible for adding a contribution of onboard still active insulin administered before the predetermined period of time and subtracting the contribution of still active insulin at the end of the predetermined period of time;

(c) a patient module that generates a patient data signal indicative of at least one patient physical parameter and a meal information signal indicative of an amount of glucose ingested by the patient during a meal;

(d) an insulin sensitivity calculator that generates an insulin sensitivity output that is indicative of an ability of insulin to stimulate glucose utilization and inhibit glucose production in the patient based on the first area under the curve [AUC(ΔCGM)] and the second area under the curve [AUC(|ΔCGM|)] signals generated by the glucose module, the insulin module area under the curve [AUC(I)], the patient data signal and the meal information signal, wherein the insulin sensitivity output (SI) is calculated as follows:

$$SI = \frac{\frac{D \cdot f}{BW} - GEZI \cdot AUC(\Delta CGM) - V_G \cdot [CGM(t_{end}) - CGM(t_{meal})]}{AUC(I) \cdot \left[\frac{AUC(|\Delta CGM|)}{(t_{end} - t_{meal})}\right]}$$

where:
D=amount of glucose ingested during the meal (in mg);
f=0.9;
BW=patient's body weight (in kg);
GEZI=a population parameter fixed to 0.01 dL/kg/min;
$V_G$=1.48 dL/kg;
$t_{end}$=ending time of study;
$t_{meal}$=starting time of study corresponding to time of the patient's last meal;
CGM($t_{end}$)=value of CGM signal at ending time of study; and
CGM($t_{meal}$)=value of CGM signal at starting time of study corresponding to time of last meal; and (e) a bolus calculator that is responsive to the insulin sensitivity output and that is configured to generate the estimated bolus dosage of insulin to be administered to the patient.

7. The system of claim 6, wherein the continuous glucose monitoring sensor comprises a self-monitoring blood glucose device.

8. The system of claim 7, wherein the continuous glucose monitoring sensor further comprises a calibration module configured to combine data from both the self-monitoring blood glucose device and the continuous glucose monitoring sensor so as to generate the glucose signal.

9. The system of claim 6, wherein the bolus calculator comprises:

(a) a carbs ratio calculator configured to calculate a carbs ratio representing a total amount of glucose entering the patient after a meal to the total amount of glucose cleared due to a pre-meal bolus;

(b) a correction factor calculator configured to calculate a correction factor representing a decrease in glucose in the patient caused by an insulin bolus; and (c) an adding circuit that adds the carbs ratio to the correction factor and that subtracts the estimated insulin on board to generate an estimated bolus dosage value.

* * * * *

UNITED STATES PATENT AND TRADEMARK OFFICE
CERTIFICATE OF CORRECTION

PATENT NO. : 9,486,172 B2  
APPLICATION NO. : 13/661755  
DATED : November 8, 2016  
INVENTOR(S) : Cobelli et al.

Page 1 of 1

It is certified that error appears in the above-identified patent and that said Letters Patent is hereby corrected as shown below:

In the Specification

Column 1, Line 11 - Please insert:
-- STATEMENT OF GOVERNMENT INTEREST
This invention was made with government support under DK085516 awarded by the National Institutes of Health. The government has certain rights in the invention. --

Signed and Sealed this
Twenty-third Day of May, 2017

Michelle K. Lee
*Director of the United States Patent and Trademark Office*